United States Patent
Oyama et al.

(10) Patent No.: US 12,357,969 B2
(45) Date of Patent: Jul. 15, 2025

(54) OXIDE CATALYST AND METHOD FOR PRODUCING UNSATURATED NITRILE

(71) Applicant: ASAHI KASEI KABUSHIKI KAISHA, Tokyo (JP)

(72) Inventors: Gosuke Oyama, Tokyo (JP); Yuya Oka, Tokyo (JP); Natsume Koike, Tokyo (JP); Makoto Yoshida, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 514 days.

(21) Appl. No.: 17/281,481

(22) PCT Filed: May 25, 2020

(86) PCT No.: PCT/JP2020/020461
§ 371 (c)(1),
(2) Date: Mar. 30, 2021

(87) PCT Pub. No.: WO2020/246283
PCT Pub. Date: Dec. 10, 2020

(65) Prior Publication Data
US 2021/0229077 A1    Jul. 29, 2021

(30) Foreign Application Priority Data

Jun. 6, 2019 (JP) .................. 2019-106015
Jun. 6, 2019 (JP) .................. 2019-106018

(51) Int. Cl.
| | | |
|---|---|---|
| B01J 23/30 | (2006.01) | |
| B01J 21/08 | (2006.01) | |
| B01J 23/00 | (2006.01) | |
| C07C 253/24 | (2006.01) | |

(52) U.S. Cl.
CPC .............. B01J 23/30 (2013.01); B01J 21/08 (2013.01); B01J 23/002 (2013.01); C07C 253/24 (2013.01)

(58) Field of Classification Search
CPC . B01J 23/30; B01J 21/08; B01J 23/002; B01J 35/30; B01J 2523/00; B01J 27/19; B01J 37/0045; B01J 37/009; B01J 37/031; B01J 37/088; C07C 253/24; C07C 253/26; C07C 255/08; Y02P 20/52; C07B 61/00
See application file for complete search history.

(56) References Cited

U.S. PATENT DOCUMENTS

| | | | |
|---|---|---|---|
| 10,343,146 B2 | 7/2019 | Ishii et al. | |
| 2008/0249328 A1 | 10/2008 | Kaduk et al. | |
| 2010/0240921 A1 | 9/2010 | Tateno et al. | |
| 2013/0053596 A1 | 2/2013 | Kato et al. | |
| 2013/0225862 A1 | 8/2013 | Tateno et al. | |
| 2013/0310593 A1 | 11/2013 | Ishii et al. | |
| 2015/0231604 A1* | 8/2015 | Ishii .................. | B01J 23/30 |
| | | | 558/321 |
| 2015/0343426 A1 | 12/2015 | Brazdil, Jr. et al. | |
| 2016/0354761 A1 | 12/2016 | Ishii et al. | |
| 2019/0232270 A1 | 8/2019 | Tateno et al. | |
| 2019/0262800 A1 | 8/2019 | Nagata et al. | |

FOREIGN PATENT DOCUMENTS

| | | |
|---|---|---|
| CN | 102892502 A | 1/2013 |
| CN | 104661745 A | 5/2015 |
| EP | 2 570 186 A1 | 3/2013 |
| JP | 10-330343 A | 12/1998 |
| JP | 2003-320248 A | 11/2003 |
| JP | 2010-526649 A | 8/2010 |
| JP | 2012-77039 A | 4/2012 |
| JP | 5190994 B2 | 4/2013 |
| JP | 5547057 B2 | 7/2014 |
| KR | 10-2019-0028484 A | 3/2019 |
| RU | 2 476 265 C2 | 2/2013 |
| TW | 201811434 A | 4/2018 |
| WO | WO 2012/105543 A1 | 8/2012 |

(Continued)

OTHER PUBLICATIONS

Baca et al., "Propane oxidation on MoVTeNbO mixed oxide catalysts: study of the phase composition of active and selective catalysts," Topics in Catalysis (2003), vol. 23, Nos. 1-4, pp. 39-46, total 10 pages.

(Continued)

*Primary Examiner* — Joseph K McKane
*Assistant Examiner* — Meghan C Heasley
(74) *Attorney, Agent, or Firm* — Birch, Stewart, Kolasch & Birch, LLP

(57) ABSTRACT

An oxide catalyst to be used for gas-phase catalytic ammoxidation reaction of propane or isobutane, the oxide catalyst comprising a composite oxide, wherein the composite oxide comprises a catalytically active species to be isolated from the composite oxide using a hydrogen peroxide solution, and the catalytically active species has an average composition represented by the following formula (1) in STEM-EDX measurements;

Formula:

$$Mo_1V_aSb_bNb_cW_dX_eO_n \qquad (1)$$

wherein X represents at least one selected from the group consisting of Te, Ce, Ti, and Ta; a, b, c, and d satisfy relations represented by a formulae of $0.050 \leq a \leq 0.200$, $0.050 \leq b \leq 0.200$, $0.100 \leq c \leq 0.300$, $0 \leq d \leq 0.100$, $0 \leq e \leq 0.100$, and $a \leq c$; and n represents a number determined by valences of the other elements.

11 Claims, No Drawings

(56) References Cited

FOREIGN PATENT DOCUMENTS

WO    WO 2014/050615 A1    4/2014

OTHER PUBLICATIONS

International Search Report for PCT/JP2020/020461 mailed on Jul. 28, 2020.

Millet et al., "Characterization of tellurium in MOVTeNbO catalysts for propane oxidation or ammoxidation," Applied Catalysis A: General (2002), vol. 232, pp. 77-92.

Millet et al., "Study of the valence state and coordination of antimony in MoVSbO catalysts determined by XANES and EXAFS," Applied Catalysis A: General (2003), vol. 244, pp. 359-370.

Safonova et al., "Mechanism of the Oxidation-Reduction of the MoVSbNbO Catalyst: In Operando X-ray Absorption Spectroscopy and Electrical Conductivity Measurements," J. Phys. Chem. B, 2006, vol. 110, pp. 23962-23967.

Shannon, "Revised Effective Ionic Radii and Systematic Studies of Interatomic Distances in Halides and Chalcogenides," Acta Cryst. (1976), A32, pp. 751-767, total 18 pages.

Written Opinion of the International Searching Authority for PCT/JP2020/020461 mailed on Jul. 28, 2020.

Golinska-Mazwa et al., "Niobiosilica Materials as Attractive Supports for Sb—V—O Catalysts", Top Catal, vol. 55, 2012 (Published online: Jul. 27, 2012), 837-845.

Lwin et al., "Characterization of MoVTeNbOx Catalysts during Oxidation Reactions Using In Situ/Operando Techniques: A Review", Catalysts, vol. 7, No. 109, 2017, pp. 1-15 (16 pages total).

International Preliminary Report on Patentability and Written Opinion mailed Dec. 16, 2021, in PCT/JP2020/020461.

* cited by examiner

OXIDE CATALYST AND METHOD FOR PRODUCING UNSATURATED NITRILE

TECHNICAL FIELD

The present invention relates to an oxide catalyst and a method for producing an unsaturated nitrile.

BACKGROUND ART

In the past, a composite oxide containing a plurality of metals such as molybdenum and vanadium has been utilized as a catalyst to be used in producing an unsaturated carboxylic acid or an unsaturated nitrile through gas-phase catalytic oxidation reaction or gas-phase catalytic ammoxidation reaction of propylene or isobutylene. The composite oxide containing a plurality of metals such as molybdenum and vanadium has also been utilized in the production, using propane or isobutane in place of an olefin as a starting material, of a corresponding unsaturated nitrile.

Non Patent Literature 1 describes an oxide catalyst containing molybdenum (Mo), vanadium (V), antimony (Sb), and niobium (Nb). Non Patent Literature 1 makes clear the action mechanism of oxidation-reduction of the oxide catalyst and specifically discloses a catalyst of Mo/V/Sb/Nb=1/0.33/0.15/0.11 as the oxide catalyst.

Patent Literature 1 discloses a catalyst composition for subjecting propane to ammoxidation in a gas phase, the catalyst composition containing one or more crystal phases, wherein at least one of the crystal phases is a first phase having an M1 crystal structure and containing a mixed metal oxide containing molybdenum (Mo), vanadium (V), antimony (Sb), and niobium (Nb); and the first phase has a unit lattice volume within a range of 2250 $Å^3$ to 2350 $Å^3$, a first crystal size, and a second size that crosses the first crystal size, provided that a ratio of the first size to the second size is within a range of 2.5 to 0.7. It is disclosed that the catalyst composition exhibits the ability that makes ammoxidation of a saturated hydrocarbon to a corresponding unsaturated nitrile easy with a high yield.

CITATION LIST

Patent Literature

[Patent Literature 1]: Japanese Patent No. 5547057

Non Patent Literature

[Non Patent Literature 1]: Safonova, O., et. al., J. Phys. Chem. B 2006, 110, 23962 to 23967
[Non Patent Literature 2]: Millet, J. M., et. al., Appl. Catal., A 2002, 232, 77
[Non Patent Literature 3]: Millet, J. M., et. al., Appl. Catal., A 2003, 244, 359
[Non Patent Literature 4]: Baca, M., et. al., Top. Catal. 2003, 23, 39
[Non Patent Literature 5]: Shannon et al., Acta A 32 (1976) 751

SUMMARY OF INVENTION

Technical Problem

In gas-phase catalytic ammoxidation of propane or isobutane, improving the yield of a product and increasing the productivity are problems. Non Patent Literature 1 only discloses, as mentioned above, the action mechanism of the oxidation-reduction of the oxide catalyst containing molybdenum (Mo), vanadium (V), antimony (Sb), and niobium (Nb) and having an orthorhombic crystal structure, but a study on improving the yield of an unsaturated nitrile has not been made.

Patent Literature 1 discloses that the yield of an unsaturated nitrile can be improved by controlling the aspect ratio of this oxide catalyst can be improved, but a study on controlling the ratio of elements that form the crystal structure of the oxide catalyst has not been made.

The present invention has been completed in consideration of the problems, and an object of the present invention is to provide an oxide catalyst capable of improving the yield of an unsaturated nitrile which is a product in the gas-phase catalytic ammoxidation reaction of propane or isobutane and a method for producing an unsaturated nitrile using the oxide catalyst.

Solution to Problem

The present inventors have conducted diligent studies in order to solve the problems to find that an oxide catalyst containing a composite oxide having a predetermined element ratio, specifically a composite oxide in which the content ratio of Nb is increased and the content ratio of V is relatively lowered, can improve the yield of an unsaturated nitrile, thereby completed the present invention.

That is, the present invention includes the following aspects.

[1]

An oxide catalyst to be used for gas-phase catalytic ammoxidation reaction of propane or isobutane, the oxide catalyst comprising a composite oxide, wherein
the composite oxide comprises a catalytically active species to be isolated from the composite oxide using a hydrogen peroxide solution, and
the catalytically active species has an average composition represented by the following formula (1) in STEM-EDX measurements;
Formula:

$$Mo_1V_aSb_bNb_cW_dX_eO_n \qquad (1)$$

wherein X represents at least one selected from the group consisting of Te, Ce, Ti, and Ta; a, b, c, and d satisfy relations represented by formulae of $0.050 \le a \le 0.200$, $0.050 \le b \le 0.200$, $0.100 \le c \le 0.300$, $0 \le d \le 0.100$, $0 \le e \le 0.100$, and $a \le c$; and n represents a number determined by valences of the other elements.

[2]

The oxide catalyst according to [1], wherein the formula (1) satisfies a relation represented by a formula of $1.1 \times a \le c$.

[3]

The oxide catalyst according to [1], wherein the formula (1) satisfies a relation represented by a formula of $1.3 \times a \le c$.

[4]

The oxide catalyst according to any one of [1] to [3], wherein the formula (1) satisfies a relation represented by a formula of $8.00 \le 100 \times b/(1+a) \le 10.00$.

[5]

The oxide catalyst according to any one of [1] to [4], wherein
the oxide catalyst comprises silica as a carrier carrying the complex oxide, and
a mass proportion of the silica is 30 to 70% by mass in terms of $SiO_2$ based on a total amount of the oxide catalyst.

[6]

An oxide catalyst to be used for gas-phase catalytic ammoxidation reaction of propane or isobutane, the oxide catalyst comprising a composite oxide, wherein the composite oxide comprises a catalytically active species comprising molybdenum, vanadium, antimony, and niobium, and a mass proportion of the catalytically active species is 45% by mass or more based on a total amount of the composite oxide.

[7]

A method for producing an unsaturated nitrile, the method comprising producing an unsaturated nitrile through gas-phase catalytic ammoxidation reaction of propane or isobutane in the presence of the oxide catalyst according to any one of [1] to [6].

Advantageous Effects of Invention

According to the present invention, an oxide catalyst capable of improving the yield of an unsaturated nitrile which is a product in gas-phase catalytic ammoxidation reaction of propane or isobutane and a method for producing an unsaturated nitrile using the oxide catalyst can be provided.

DESCRIPTION OF EMBODIMENTS

Hereinafter, an embodiment of the present invention (hereinafter, referred to as "present embodiment") will be described in detail. It is to be noted that the present invention is not limited to the following present embodiment and can be carried out by modifying the present embodiment variously within the scope of the present invention. In a case where numerical values or physical property values are expressed before and after "-" in such a way as to interpose "-" therebetween in the present specification, the values are used on condition that the values before and after "-" are included. For example, the notation of a numerical value range of "1 to 100" includes both of the upper limit value "100" and the lower limit value "1". The same applies to the notations of the other numerical value ranges.

[Oxide Catalyst]

An oxide catalyst of the present embodiment is used for gas-phase catalytic ammoxidation reaction of propane or isobutane and is an oxide catalyst containing a composite oxide. Hereinafter, the reaction of synthesizing an unsaturated nitrile from propane or isobutane, an oxygen source such as oxygen, and a nitrogen source such as ammonia will simply be referred to as "gas-phase catalytic ammoxidation reaction".

The oxide catalyst of the present embodiment contains a predetermined composite oxide and, if necessary, may contain a carrier carrying the composite oxide. Hereinafter, each component will be described in detail.

(Composite Oxide)

The composite oxide contains a catalytically active species to be isolated from the composite oxide using a hydrogen peroxide solution, and the catalytically active species has an average composition represented by the following formula (1) in STEM-EDX measurements.

Formula:

$$Mo_1V_aSb_bNb_cW_dX_eO_n \quad (1)$$

wherein X represents at least one selected from the group consisting of Te, Ce, Ti, and Ta; a, b, c, and d satisfy relations represented by formulae of 0.050≤a≤0.200, 0.050≤b≤0.200, 0.100≤c≤0.300, 0≤d≤0.100, 0≤e≤0.100, and a≤c; and n represents a number determined by valences of the other elements.

The catalytically active species in the present embodiment can be isolated from the oxide catalyst, more specifically from the composite oxide, using a hydrogen peroxide solution, and the substance thus isolated is referred to as the catalytically active species. On this occasion, in a case where the oxide catalyst contains a carrier, the catalytically active species may be isolated in a state in which the carrier is mixed, but the carrier and the catalytically active species are each a different component. The average composition of the isolated catalytically active species can be measured by STEM-EDX. STEM-EDX herein is a scanning transmission electron microscope equipped with an energy dispersive characteristic X-ray spectrometer.

The catalytically active species herein is a crystal phase containing at least molybdenum (Mo), vanadium (V), antimony (Sb), and niobium (Nb) and a composite metal oxide having catalytic activity for subjecting propane and/or isobutane to ammoxidation. It is to be noted that if necessary, at least one additional metal (X) selected from the group consisting of tungsten (W), tellurium (Te), cerium (Ce), titanium (Ti), and tantalum (Ta) may further be contained in the catalytically active species.

The previously mentioned catalytically active species is described as the first phase having an M1 crystal structure in Patent Literature 1 (Japanese Patent No. 5547057) for example, and similar explanation is made in Non Patent Literature 1 (Safonova, O., et. al., J. Phys. Chem. B 2006, 110, 23962 to 23967), Non Patent Literature 2 (Millet, J. M., et. al., Appl. Catal., A 2002, 232, 77), Non Patent Literature 3 (Millet, J. M., et. al., Appl. Catal., A 2003, 244, 359), Non Patent Literature 4 (Baca, M., et. al., Top. Catal. 2003, 23, 39), and the like.

As a result of diligent studies by the present inventors, it has been made clear that by using an oxide catalyst in which the content ratio of Nb in the catalytically active species is increased and the content ratio of V is relatively reduced, an improvement in the yield of an unsaturated nitrile in the gas-phase catalytic ammoxidation reaction is achieved. That is, when the formula (1) of the catalytically active species has the above-described average composition, the yield of an unsaturated nitrile to be obtained through the gas-phase catalytic ammoxidation reaction is thereby improved.

As will be mentioned later in the method for producing an oxide catalyst, it has been found that by using a particular Nb-containing liquid as a starting material or/and further performing a particular catalyst production step, the content ratio of Nb in the catalytically active species can be increased and the content ratio of V can be relatively reduced. According to Non Patent Literature 5 (Shannon et al., Acta A 32 (1976) 751), the ion radii of Nb and V (in a case of five valences and six-coordination in an oxide) are 0.64 and 0.54 Å, respectively, and there is a large difference, as large as 18.5%, between them, and therefore it is generally considered that a substitutional solid solution is hardly formed by Hume-Rothery rules. The Hume-Rothery rules herein are rules showing that, in substitutional solid solutions, a solid solution is formed almost all over the component ratio if the difference in the ionic radius of respective components is up to about 10%, but on the other hand, in a case where the ionic radii are different by 15% or more, a solid solution is hardly formed. It is inferred that specific substitution phenomena, such as that the site which Mo, having an ionic radius of 0.59 Å, the ionic radius being such that the difference in the ionic radius is relatively small from both of Nb and V (Nb: 8.5%), occupies is substituted with Nb, and that the destabilized, adjacent site which V has occupied is substituted with Mo, due to the fact that the present catalytically active species has an extremely complicated crystal structure have occurred, although the detailed substitution structure is not clearly understood.

The factor that can improve the yield of an unsaturated nitrile by increasing the content ratio of Nb in the catalytically active species and relatively reducing the content ratio of V is considered as follows. First of all, Nb has a high melting point, and when the content ratio of Nb having a high melting point is increased, the stability of the catalytically active species is improved in a reaction atmosphere. It is considered that the yield of an unsaturated nitrile can thereby be improved.

In the present embodiment, it is preferable to relatively increase the content ratio of Sb with respect to the content ratio of Mo—O—V in the catalytically active species as compared to that in conventional catalysts. Thereby, the content ratio of Mo—O—V, which is considered to cause non-selective decomposition activity although Mo—O—V is an active spot of dehydrogenation reaction of propane or isobutane, can be relatively reduced and the content ratio of Sb, which is an active spot of the gas-phase catalytic ammoxidation reaction, can be relatively increased. It is considered that the yield of an unsaturated nitrile can therefore be improved.

The unsaturated nitrile indicates acrylonitrile as a preferred aspect of the present embodiment.

The composite oxide in the present embodiment is a metal oxide that constitutes the oxide catalyst of the present embodiment. At least molybdenum (Mo), vanadium (V), antimony (Sb), and niobium (Nb) are contained as the metals of the metal oxide, and if necessary, an additional metal may be contained.

The catalytically active species in the present embodiment indicates metal components which are obtained by performing a treatment with hydrogen peroxide as shown in the above-described method, specifically the method of measuring (physical property 1), which will be mentioned later. Usually, a complex oxide contains two crystal phases and an amorphous component in many cases. These two crystal phases are constituted by a phase having strong oxidation resistance and a phase having weak oxidation resistance, and it is known that in the present catalyst system, the phase having strong oxidation resistance corresponds to the catalytically active species, as described in Non Patent Literature 1. When a pre-treatment using a hydrogen peroxide solution is performed on the composite oxide, the phase having weak oxidation resistance is dissolved, but the catalytically active species which is a phase having strong oxidation resistance is not dissolved, so that the state before the oxidation treatment can be retained. Therefore, by performing the oxidation treatment, the phase having weak oxidation resistance is dissolved, so that the catalytically active species can be isolated from the composite oxide, and the composition of the catalytically active species can be measured with high accuracy.

As shown in the method of measuring (physical property 4), which will be mentioned later, the mass proportion of the catalytically active species ($G_1$) assuming that the weight of the composite oxide is 100% can be calculated using the following equation from the mass proportion of the carrier in which an increase or decrease in weight is hardly observed before and after the treatment. The mass proportion of the catalytically active species is preferably 43% by mass or more, more preferably 45% by mass or more, and still more preferably 48% by mass or more in terms of weight fraction.

$$J_1 = \frac{100 \times (100 - I_2) \times I_1}{(100 - I_1) \times I_2}$$

$I_1$: Mass proportion of carrier in oxide catalyst
$I_2$: Mass proportion of carrier in residue of oxide catalyst obtained by oxidation treatment with hydrogen peroxide solution The catalytically active species may further contain or does not have to contain an additional metal element (X). Examples of the additional metal element (X) include, but not particularly limited to, Te, Ce, Ti, and Ta. In a case where the catalytically active species contains an additional metal element (X), the additional metal element (X) may be one metal element or may be a plurality of metal elements. It is to be noted that in a case where the catalytically active species does not contain an additional metal element (X), the formula (1) is represented as the following formula (1a).

$$Mo_1V_aSb_bNb_cW_dO_n \qquad (1a)$$

wherein a, b, c, d, and n have the same meaning as those in the formula (1).

With respect to the measurement of the average composition of the catalytically active species, the catalytically active species is isolated from the oxide catalyst using a hydrogen peroxide solution, and the average composition of the isolated catalytically active species can be measured by STEM-EDX, as mentioned above, and specifically, the measurement of the average composition of the catalytically active species can be performed by the method (physical property 1) described in Examples.

In the formula (1), a satisfies $0.050 \leq a \leq 0.200$, preferably satisfies $0.050 \leq a \leq 0.150$, more preferably satisfies $0.080 \leq a \leq 0.150$, still more preferably satisfies $0.100 \leq a \leq 0.150$, and further still more preferably satisfies $0.100 \leq a \leq 0.130$.

In the formula (1), b satisfies $0.050 \leq b \leq 0.200$, preferably satisfies $0.050 \leq b \leq 0.150$, more preferably satisfies $0.070 \leq b \leq 0.150$, and still more preferably satisfies $0.080 \leq b \leq 0.150$.

In the formula (1), c satisfies $0.100 \leq c \leq 0.300$, preferably satisfies $0.100 \leq c \leq 0.250$, more preferably satisfies $0.130 \leq c \leq 0.250$, and still more preferably satisfies $0.140 \leq c \leq 0.200$.

In the formula (1), d satisfies $0 \leq d \leq 0.100$, preferably satisfies $0 \leq d \leq 0.100$, more preferably satisfies $0.010 \leq d \leq 0.100$, and still more preferably satisfies $0.020 \leq d \leq 0.100$.

In the formula (1), e satisfies $0 \leq e \leq 0.100$, preferably satisfies $0 \leq e \leq 0.050$, more preferably satisfies $0 \leq e \leq 0.010$, and still more preferably satisfies $e=0$. It is to be noted that e represents a content ratio of at least one metal X selected from the group consisting of Te, Ce, Ti, and Ta to one atom of molybdenum, and in a case where two or more metals X are contained, e represents the total content ratio of the metals X.

There is a tendency that when each of a, b, c, d, and e satisfies the above-described range, thereby the yield of an unsaturated nitrile is more improved. The average composition of the catalytically active species can be controlled by adjusting the amount of starting material components containing the elements in producing the oxide catalyst. Satisfying the relation represented by a formula a≤c in particular can be controlled by using a particular Nb-containing liquid as a starting material.

The formula (1) preferably satisfies $0.050 \leq a \leq 0.150$ and $0.100 \leq c \leq 0.250$, and more preferably satisfies $0.050 \leq a \leq 0.150$, $0.080 \leq b \leq 0.150$, $0.100 \leq c \leq 0.250$, and $0 \leq d \leq 0.100$. In addition, the formula (1) preferably satisfies $0.050 \leq a \leq 0.150$, $0.100 \leq c \leq 0.250$, and $e=0$, and more preferably satisfies $0.050 \leq a \leq 0.150$, $0.08 \leq b \leq 0.150$, $0.100 \leq c \leq 0.250$, $0 \leq d \leq 0.100$, and $e=0$. There is a tendency that when the formula (1) satisfies the above-described composition, thereby the yield of an unsaturated nitrile is more improved.

The formula (1) satisfies the relation represented by a formula of $a \leq c$, and from the viewpoint of further improving the yield of an unsaturated nitrile, preferably satisfies a relation represented by a formula of $1.1 \times a \leq c$, more preferably satisfies a relation represented by a formula of $1.3 \times a \leq c$, and still more preferably satisfies a relation represented by a formula of $1.5 \times a \leq c$. In addition, the formula (1) preferably satisfies a relation represented by a formula of $c \leq a \times 3.0$, more preferably satisfies a relation represented by a formula of $c \leq a \times 2.5$, and still more preferably satisfies a relation represented by a formula of $c \leq a \times 2.0$.

Sb contained in the catalytically active species is considered to be an active spot of the gas-phase catalytic ammoxidation reaction, as mentioned above, and therefore is preferably contained in a certain amount. Specifically, the formula (1) preferably satisfies a relation represented by a formula of $0.100 \leq b/(a+b+c) \leq 0.400$, more preferably satisfies a relation represented by a formula of $0.150 \leq b/(a+b+c) \leq 0.300$, and still more preferably satisfies a relation represented by a formula of $0.200 \leq b/(a+b+c) \leq 0.300$. There is a tendency that when the formula (1) satisfies the above-described relation, thereby the yield of an unsaturated nitrile is more improved.

The catalytically active species preferably contains a certain amount of Sb, the formula (1) preferably satisfies a relation represented by a formula of $7.00 \leq 100 \times b/(1+a) \leq 11.00$, more preferably satisfies a relation represented by a formula of $8.00 \leq 100 \times b/(1+a) \leq 10.00$, and still more preferably satisfies a relation represented by a formula of $8.50 \leq 100 \times b/(1+a) \leq 10.00$. The yield of an unsaturated nitrile tends to be improved more when the formula (1) satisfies the above-described relation.

(Carrier)

The oxide catalyst of the present embodiment may contain a carrier in addition to the composite oxide. That is, the oxide catalyst of the present embodiment may take a form such that the oxide catalyst is carried by the carrier. As the carrier, an oxide such as silica, alumina, titania, or zirconia is used, but silica is suitable from the viewpoint that lowering of the selectivity for an object is small, and the wear resistance and particle strength of the formed catalyst particle are made satisfactory.

The amount of the silica carrier is usually 20% by mass to 80% by mass, preferably 30% by mass to 70% by mass, and more preferably 40% by mass to 60% by mass based on the total mass of the silica carrier and the composite oxide, namely the total amount of the oxide catalyst.

One of the preferred aspects of the oxide catalyst of the present embodiment is the oxide catalyst containing silica as a carrier carrying the composite oxide, and the mass proportion of the silica is 30% by mass to 70% by mass in terms of $SiO_2$ based on the total amount of the oxide catalyst.

Examples of the starting material for the silica carrier include, but not particularly limited to, silica sol (also called colloidal silica) and powdery silica. As the starting material for the silica carrier, silica sol is preferable from the viewpoint of easiness of handling. The average primary particle diameter of silica contained in silica sol is not particularly limited. As the silica carrier, different types of silica sol each having a different primary particle diameter may be mixed for use.

The shape and particle size of the oxide catalyst of the present embodiment are not particularly limited, but in a case where the oxide catalyst of the present embodiment is used as a fluidized bed catalyst, the oxide catalyst is preferably spherical and preferably has a particle diameter of 10 to 150 μm from the viewpoint of fluidity.

[Method for Producing Oxide Catalyst]

The oxide catalyst of the present embodiment can be produced by a production method including: a starting material compounding step of appropriately compounding starting materials, thereby obtaining a precursor slurry; a drying step of drying the precursor slurry, thereby obtaining a dried particle; and a calcination step of calcining the dried particle, thereby obtaining the oxide catalyst. If necessary, the method for producing the oxide catalyst of the present embodiment may include a removal step of removing a protrusion of the obtained oxide catalyst.

It is to be noted that hereinafter, aqueous mixed liquid A corresponds to mixed liquid (B) not containing niobium in basic applications (Japanese Patent Application No. 2019-106015 and Japanese Patent Application No. 2019-106018). Niobium starting material liquid B corresponds to the composition for producing a catalyst, containing niobium, composition (A) for producing a catalyst, or the mixed liquid in basic applications (Japanese Patent Application No. 2019-106015 and Japanese Patent Application No. 2019-106018). Precursor slurry C corresponds to the precursor slurry or the starting material-compounded liquid in basic applications (Japanese Patent Application No. 2019-106015 and Japanese Patent Application No. 2019-106018).

(Starting Material Compounding Step)

The starting material compounding step is not particularly limited, and for example, includes: preparation step A of mixing a molybdenum starting material, a vanadium starting material, an antimony starting material, and water, thereby preparing aqueous mixed liquid A; preparation step B of mixing a niobium starting material and an organic acid, thereby preparing niobium starting material liquid B; and mixing step C of mixing aqueous mixed liquid A and niobium starting material liquid B, thereby preparing precursor slurry C.

The oxide catalyst of the present embodiment can be produced by adopting a preferred preparation condition, which will be mentioned later, in preparation step B or by adopting a preferred mixing condition, which will be mentioned later, in mixing step C.

Next, niobium starting material liquid B containing an organic acid and a niobium starting material and aqueous mixed liquid A, which have been prepared in preparation step B in advance, are mixed to match the intended composition, thereby obtaining a starting material-compounded liquid as a precursor slurry (mixing step C). For example, in a case where the catalyst contains W or Ce, the starting material-compounded liquid is obtained by suitably mixing a compound containing W. The compound containing W or Ce can be added in aqueous mixed liquid A, or can be added simultaneously in mixing niobium starting material liquid B and aqueous mixed liquid A.

In a case where the oxide catalyst contains a silica carrier, namely in a case where the oxide catalyst is carried by a silica carrier, a starting material-compounded liquid can be prepared in such a way as to contain silica sol, and in this case, silica sol can appropriately be added.

(Preparation Step A)

Preparation step A is a step of mixing a molybdenum starting material, a vanadium starting material, an antimony starting material, and water, thereby preparing aqueous mixed liquid A. More specifically, the molybdenum starting material, the vanadium starting material, and the antimony starting material are added to water and heated at a predetermined temperature or higher under stirring, and aqueous mixed liquid A can thereby be prepared. On this occasion, in a case where the catalyst contains W or Ce, a tungsten starting material or a cerium starting material may further be added.

The component starting materials to be used for aqueous mixed liquid A are not particularly limited, and for example, the following compounds can be used.

Examples of the molybdenum starting material include, but not particularly limited to, molybdenum oxide, ammonium dimolybdate, ammonium heptamolybdate, phosphomolybdic acid, and silicomolybdic acid, and among others, ammonium heptamolybdate can suitably be used.

Examples of the vanadium starting material include, but not particularly limited to, vanadium pentoxide, ammonium metavanadate, and vanadyl sulfate, and among others, ammonium metavanadate can suitably be used.

As the antimony starting material, an oxide of antimony can suitably be used. The tungsten starting material is not particularly limited, and for example, ammonium metatungstate is suitably used. The cerium starting material is not particularly limited, and for example, cerium nitrate hexahydrate is suitably used.

The lower limit of the temperature during stirring is usually 80° C. or higher, and is preferably 90° C. or higher. There is a tendency that when the temperature during stirring is set to 80° C. or higher, thereby the oxidation/reduction reaction between the oxide of antimony, which is, in general, hardly soluble to water, and another oxide starting material (for example, vanadium starting material) is more facilitated. On the other hand, it is preferable that the upper limit of the temperature during stirring be usually 100° C. or lower in order to avoid bumping.

(Preparation Step B)

Preparation step B is a step of mixing a niobium starting material and an organic acid, thereby preparing niobium starting material liquid B. In preparation step B, water may further be mixed. The niobium starting material is hardly soluble in general and is therefore dissolved in water by allowing the organic acid to coexist. On this occasion, it is preferable that the Nb content in niobium starting material liquid B be high, and the dispersibility of Nb be satisfactory in the preparation of the oxide catalyst of the present embodiment.

From such a viewpoint, it is preferable to mix the niobium starting material and the organic acid under stirring and heating in preparation step B while adjusting the molar ratio of the organic acid to Nb and the turbidity. More specifically, by setting the molar ratio of the organic acid to Nb (organic acid/Nb) to 2.40 or less, the Nb concentration can sufficiently be increased, and the use amount of the organic acid that functions as a reducing agent can sufficiently be reduced. In addition, by setting the turbidity of niobium starting material liquid B to 500 NTU or less, the dispersibility of Nb can be retained satisfactorily even though a sufficiently high concentration of Nb is contained. Due to niobium starting material liquid B which is obtained in this way, the content ratio of Nb in the composite oxide in the oxide catalyst of the present embodiment is increased, and the content ratio of V, which is considered to cause the decomposition activity of an alkane, is relatively lowered, and the yield of an unsaturated nitrile can thereby be increased.

The niobium starting material is not particularly limited as long as it is a compound containing Nb, but any of such compounds is hardly soluble and therefore is dissolved by allowing the organic acid to coexist. Specific examples of the niobium starting material include, but not limited to, niobium hydrogen oxalate, ammonium niobium oxalate, $NbCl_3$, $NbCl_5$, $Nb_2(C_2O_4)_5$, $Nb_2O_5$, niobic acid, $Nb(OC_2H_5)_5$, a halide of niobium, a halogenated ammonium salt of niobium, and combinations thereof. Among these, in a case where an additional metal is added to niobium starting material liquid B, niobic acid and niobium hydrogen oxalate are preferable from the viewpoint of reducing an influence on the additional metal. It is to be noted that niobic acid contains niobium hydroxide and niobium oxide. The niobium starting material changes in quality in some cases due to long-term storage or progress of dehydration, and therefore a niobium starting material immediately after production is preferably used for preparing niobium starting material liquid B, but a compound which has somewhat undergone a change in quality may be used.

The niobium starting material may be a solid or may take the form of suspension in preparing niobium starting material liquid B. In a case where niobic acid is used, the particle diameter is preferably smaller from the viewpoint of easiness of dissolution. Niobic acid can be washed with ammonia water and/or water before use.

Examples of the organic acid include, but not particularly limited to, a dicarboxylic acid. Specific examples of the dicarboxylic acid include oxalic acid, malonic acid, succinic acid, and glutaric acid, and from the viewpoint of suppressing over-reduction of the metal oxide in the calcination stage at the time of producing the catalyst, oxalic acid is preferable, more specifically, an oxalic anhydride and oxalic acid dihydrate are preferable. Only one dicarboxylic acid may be added, or a plurality of dicarboxylic acids may be combined.

As mentioned above, the molar ratio of the organic acid to Nb (organic acid/Nb) is preferably low. When the value of the molar ratio (organic acid/Nb) is larger, the Nb concentration is lower, and there is a tendency that the dispersibility and stability of Nb in niobium starting material liquid B are satisfactory, but when the value of the molar ratio (organic acid/Nb) is excessively large, there is a risk that a resultant catalyst is over-reduced by an influence of the organic acid that functions as a reducing agent, moreover, the amount of Nb is deficient, thereby the catalytically active species to be an active spot is not formed sufficiently, and an effect of suppressing decomposition of a product is not obtained sufficiently. On the other hand, when the value of the molar ratio (organic acid/Nb) is smaller, the Nb concentration is higher, niobium starting material liquid B containing a sufficient amount of Nb is made, but the dispersibility of Nb in niobium starting material liquid B is lowered, and as a result, uniform introduction of Nb into the catalytically active species is made difficult. From such a viewpoint, the molar ratio (organic acid/Nb) is set to 2.40 or less. That is, by setting the molar ratio to 2.40 or less, a sufficient amount of Nb can be introduced without making the introduction amount of the organic acid that functions as a reducing agent excessive, and therefore the catalytically active species to be an active spot is formed sufficiently, and the effect of suppressing the decomposition of a product can sufficiently be obtained, and as a result, the performance of a resultant catalyst is made satisfactory. From the viewpoint of which is similar to the viewpoint described above, the molar ratio (organic acid/Nb) is preferably 2.20 or less, more preferably 1.90 or more and 2.18 or less, and still more preferably 1.95 or more and 2.15 or less.

As mentioned previously, if the dispersibility of Nb in niobium starting material liquid B is not in a satisfactory state, precipitation of Nb is observed, and there is a tendency that a change in the value of the Nb concentration with time is remarkable. Therefore, the molar ratio in the present embodiment is evaluated based on the concentration after niobium starting material liquid B is left standing at normal temperature for one day from immediately after the preparation. It is to be noted that the "normal temperature" in the present specification means a temperature around 15 to 25° C. Specifically, the molar ratio can be measured by the method described in Examples, which will be mentioned later. The molar ratio (organic acid/Nb) can be adjusted in the above-described range by the ratios of the starting materials to be used.

With respect to the turbidity of niobium starting material liquid B, a larger value suggests that the dispersibility of Nb is worse, and a smaller value suggests that the dispersibility of Nb is more satisfactory. From such a viewpoint, the turbidity of niobium starting material liquid B is 500 NTU or less. In the present embodiment, the turbidity is sufficiently low even though the molar ratio (organic acid/Nb) is reduced to as low as 2.40 or less, as mentioned previously, and therefore the catalytically active species to be an active spot is formed sufficiently, and the effect of suppressing the decomposition of a product can sufficiently be obtained. In addition to this, uniform introduction of Nb into the catalytically active species is made possible due to satisfactory dispersibility of Nb, and as a result, the performance of a resultant oxide catalyst is made especially satisfactory. From the viewpoint similar to that described above, the turbidity is preferably 0.5 NTU or more and 400 NTU or less, and more preferably 1.0 NTU or more and 200 NTU or less.

As mentioned previously, if the dispersibility of Nb in niobium starting material liquid B is not in a satisfactory state, precipitation of Nb is observed, and there is a tendency that a change in the value of the turbidity with time is remarkable. Therefore, the turbidity in the present embodiment is also evaluated based on the turbidity after niobium starting material liquid B is left standing at normal temperature for one day from immediately after the preparation. Specifically, the turbidity can be measured by the method described in Examples, which will be mentioned later. The turbidity can be adjusted in the above-described range by adopting the preferred production method which will be mentioned later.

The mixing temperature in preparation step B is preferably higher than 60° C. and lower than 80° C., more preferably 63° C. or higher and 78° C. or lower, and still more preferably 65° C. or higher and 75° C. or lower. By setting the mixing temperature in such a way as to be higher than 60° C., there is a tendency that sufficient dispersion of Nb is facilitated. By setting the mixing temperature in such a way as to be lower than 80° C., a complex of the organic acid and Nb, which is formed in niobium starting material liquid B, is stabilized, so that there is a tendency that sufficient dispersibility is secured even though the concentration of Nb is high. In addition, stirring is preferably performed simultaneously with the heating in preparation step B. Thereby, the molar ratio (organic acid/Nb) is controlled in the above-described range, and the turbidity can be kept low.

With respect to the mixing time in preparation step B, it is desirable to take a sufficiently long reaction time from the viewpoint of allowing the reaction between the organic acid and the niobium starting material to progress sufficiently, but if the reaction time is too long, there is concern that the stability of the complex of the organic acid and Nb is lowered because the mixed liquid is exposed to a warmed state for an excessively long time. From the viewpoint of securing sufficient dispersibility even though the concentration of Nb is high, a dissolution step is preferably carried out in 1 hour or longer and 8 hours or shorter, more preferably 3 hours or longer and 7 hours or shorter, and still more preferably 4 hours or longer and 6 hours or shorter.

In a case where the organic acid and the niobium starting material are heated under stirring, the temperature of the mixture of the organic acid and the niobium starting material is decreased to 5° C. or lower, and a solid is then filtrated and separated by suction filtration to make niobium starting material liquid B.

Among those described above, it is preferable to set the molar ratio of the organic acid to Nb to 2.40 or less as organic acid/Nb and to mix the organic acid and the niobium starting material at 80° C. or lower under stirring from the viewpoint of more efficiently obtaining the oxide catalyst of the present embodiment. A condition that satisfies these is referred to as preparation condition b.

(Mixing Step C)

Mixing step C is a step of mixing aqueous mixed liquid A and niobium starting material liquid B, thereby preparing precursor slurry C. In mixing step C, if necessary, hydrogen peroxide, a basic aqueous solution, an additional metal starting material such as a tungsten starting material or a cerium starting material, and/or a carrier starting material may further be mixed. Precursor slurry C which is obtained in this way is a uniform mixed liquid in some cases, but is usually a slurry.

The mixing condition in mixing step C is not particularly limited, but, for example, the mixing temperature is preferably 50° C. or higher and 80° C. or lower, and more preferably 60° C. or higher and 80° C. or lower. The stirring time is preferably 1 hour or longer and 5 hours or shorter.

Examples of the method of adding hydrogen peroxide in mixing step C include: a method in which aqueous mixed liquid A and hydrogen peroxide are mixed and then further niobium starting material liquid B is mixed; a method in which niobium starting material liquid B and hydrogen peroxide are mixed and then further aqueous mixed liquid A is mixed; a method in which aqueous mixed liquid A, niobium starting material liquid B, and hydrogen peroxide are simultaneously mixed; and a method in which aqueous mixed liquid A and niobium starting material liquid B are mixed, and then further hydrogen peroxide is mixed. Among these, the method in which aqueous mixed liquid A and hydrogen peroxide are mixed and then further niobium starting material B is mixed is preferable.

In a case where hydrogen peroxide is added in mixing step C, the molar ratio of hydrogen peroxide to antimony (Sb) ($H_2O_2$/Sb) in aqueous mixed liquid A is preferably 0.01 or more and 5.0 or less, more preferably 2.0 or more and 4.0 or less, and still more preferably 2.5 or more and 3.5 or less. In a case where aqueous mixed liquid A and hydrogen peroxide are mixed, it is preferable to add hydrogen peroxide while stirring aqueous mixed liquid A under a heating condition.

On this occasion, the temperature is usually 30° C. to 70° C., preferably 60° C. or higher. The stirring time is preferably 30 minutes to 2 hours.

Examples of the method of adding the basic aqueous solution in mixing step C include: a method in which aqueous mixed liquid A and the basic aqueous solution are mixed and then further niobium starting material liquid B is mixed; a method in which niobium starting material liquid B and the basic aqueous solution are mixed and then further aqueous mixed liquid A is mixed; a method in which aqueous mixed liquid A, niobium starting material liquid B, and the basic aqueous solution are simultaneously mixed; and a method in which aqueous mixed liquid A and niobium starting material liquid B are mixed and then further the basic aqueous solution is mixed. Among these, the method in which aqueous mixed liquid A and niobium starting material liquid B are mixed and then further the basic aqueous solution is mixed is preferable.

Examples of the basic aqueous solution to be added in mixing step C include, but not particularly limited to, ammonia water, an amine, and an alkali aqueous solution. Among these, the basic aqueous solution is most preferably ammonia water because the ammonia water evaporates for the most part in the drying step and does not affect the steps after the drying step.

In a case where the basic aqueous solution is added in mixing step C, the molar ratio of $NH_3$ to niobium (Nb) in niobium starting material liquid B ($NH_3$/Nb) is preferably 0.01 or more and 5 or less, more preferably 2.0 or more and 4 or less, and still more preferably 2.5 or more and 3.5 or less.

Among those described above, it is preferable to mix hydrogen peroxide in such a way that the molar ratio of hydrogen peroxide to antimony (Sb) ($H_2O_2$/Sb) is 2.5 or more and to mix ammonia in such a way that the molar ratio of ammonia to niobium (Nb) ($NH_3$/Nb) is 2.0 or more in mixing step C from the viewpoint of more efficiently obtaining the oxide catalyst of the present embodiment. In addition, it is preferable to set pH in mixing step C to 5 or more and to obtain the precursor slurry by performing stirring under a heating condition of 60° C. or higher. The condition that satisfies these is referred to as mixing condition c. It is to be noted that pH can be adjusted using the above-mentioned basic aqueous solution.

Examples of the method of adding an additional metal starting material such as a tungsten starting material or a cerium starting material in mixing step C include: a method in which aqueous mixed liquid A and the additional metal starting material are mixed and then further niobium starting material liquid B is mixed; a method in which niobium starting material liquid B and the additional metal starting material are mixed and then further aqueous mixed liquid A is mixed; a method in which aqueous mixed liquid A, niobium starting material liquid B, and the additional metal starting material are simultaneously mixed; and a method in which aqueous mixed liquid A and niobium starting material liquid B are mixed and then further the additional metal starting material is mixed.

Examples of the method of adding the carrier starting material in mixing step C include: a method in which aqueous mixed liquid A and the carrier starting material are mixed and then further niobium starting material liquid B is mixed; a method in which niobium starting material liquid B and the carrier starting material are mixed and then further aqueous mixed liquid A is mixed; a method in which aqueous mixed liquid A, niobium starting material liquid B, and the carrier starting material are simultaneously mixed; and a method in which aqueous mixed liquid A and niobium starting material liquid B are mixed and then further the carrier starting material is mixed.

In a case where the oxide catalyst such that the composite oxide is carried by the silica carrier is obtained, silica sol can be used as the carrier starting material.

(Other Conditions)

By adopting both of the above-described preparation condition b and mixing condition c, the oxide catalyst satisfying the above-mentioned relations represented by formulae is obtained. Particularly, adopting both of the above-described preparation condition b and mixing condition c is preferable because the oxide catalyst satisfying the relation represented by a formula 1.1×a≤c or 1.5×a≤c, or the relation represented by a formula 8.00≤100×b/(1+a)≤10.00 can be obtained.

It is preferable that the amount of the vanadium starting material contained in aqueous mixed liquid A be relatively lower based on the amount of the niobium starting material contained in niobium starting material liquid B in addition to adopting the above-described preparation condition b or mixing condition c. Specifically, the atomic ratio V/Nb of the vanadium atom contained in the vanadium starting material to the niobium atom contained in the niobium starting material is preferably 2.7 or less, more preferably 2.0 or less, and still more preferably 1.7 or less. The atomic ratio V/Nb can be adjusted by each concentration of the vanadium starting material in aqueous mixed liquid A and the niobium starting material in niobium starting material liquid B or a mixing ratio of aqueous mixed liquid A to niobium starting material liquid B.

(Drying Step)

The drying step is a step of drying precursor slurry C obtained in the above-mentioned step, thereby obtaining a dried powder. The drying can be performed by a known method, and can be performed by, for example, spray drying or evaporation to dryness. Among these, a fine spherical dried particle is preferably obtained by spray drying. Nebulization in the spray drying method can be performed by a centrifugal system, a two-fluid nozzle system, or a high-pressure nozzle system. As the heat source for drying, steam, or air heated with an electric heater or the like can be used. The inlet temperature of a drier in a spray drying apparatus is preferably 150 to 300° C., and the outlet temperature of the drier is preferably 100 to 160° C.

(Calcination Step)

The calcination step is a step of calcining the dried powder obtained in the drying step, thereby obtaining the oxide catalyst. As a calcination apparatus, a rotary furnace (rotary kiln) can be used. The shape of a calciner is not particularly limited, but is preferably a tubular shape because continuous calcination can be carried out. The shape of a calcination pipe is not particularly limited, but is preferably cylindrical. As a heating system, an external heating type is preferable, and an electric furnace can suitably be used.

Appropriate size, material, and the like of a calcination pipe can be selected according to the calcination condition or the production amount, but the inner diameter of the calcination pipe is preferably 70 to 2000 mm, more preferably 100 to 1200 mm, and the length of the calcination pipe is preferably 200 to 10000 mm, and more preferably 800 to 8000 mm. In a case where shock is given to the calciner, the thickness of the calciner is preferably 2 mm or more, and more preferably 4 mm or more from the viewpoint of having a sufficient thickness to such an extent that the calciner is not broken by the shock, and is preferably 100 mm or less, and more preferably 50 mm or less from the viewpoint of sufficiently transmitting the shock to the inside of the calciner. The material of the calciner is not particularly limited, except that the material has heat resistance and strength such that the material does not broken by the shock, and SUS can suitably be used.

The calcination pipe can be divided into two or more zones by installing, in the calcination pipe, a weir plate vertically to the flow of a powder, the weir plate having a hole for allowing the powder to pass in the central portion. Installing the weir plate makes it easy to secure the retention time in the calcination pipe. The number of the weir plates may one or plural. The material of the weir plate is preferably a metal, and the same material as that of the calcination pipe can suitably be used. The height of the weir plate can be adjusted according to the retention time to be secured. For example, in a case where a powder is supplied at 250 g/hr in a rotary furnace having a SUS calcination pipe with an inner diameter of 150 mm and a length of 1150 mm, the weir plate is preferably 5 to 50 mm, more preferably 10 to 40 mm, and still more preferably 13 to 35 mm. The thickness of the weir plate is not particularly limited and is preferably adjusted according to the size of the calcination pipe. For example, in the case of a rotary furnace having a SUS calcination pipe with an inner diameter of 150 mm and a length of 1150 mm, the thickness of the calcination pipe is preferably 0.3 mm or more and 30 mm or less, and more preferably 0.5 mm or more and 15 mm or less.

The calcination pipe is preferably rotated in order to prevent crazing, cracking, and the like of the dried powder and to perform calcination uniformly. The rotation speed of the calcination pipe is preferably 0.1 to 30 rpm, more preferably 0.5 to 20 rpm, and still more preferably 1 to 10 rpm.

When the dried powder is calcined, it is preferable that raising the temperature for heating the dried powder be started from a temperature lower than 400° C., and the temperature be raised continuously or intermittently up to a temperature within a range of 550 to 800° C.

The calcination atmosphere may be under an air atmosphere or under an air flow, but it is preferable to carry out at least part of the calcination while allowing an inert gas, such as nitrogen, which is substantially free of oxygen, to flow. The supply amount of the inert gas is 50 N litters or more, preferably 50 to 5000 N litters, and still more preferably 50 to 3000 N litters per kg of the dried powder (N litters mean litters measured under the standard temperature/pressure condition, namely litters measured at 0° C. and 1 atm). On this occasion, there is no problem when the inert gas and the dried powder are brought into contact in a parallel flow or a counter flow, but counterflow contact is preferable in consideration of gas components generated from the dried powder and the air which is mixed in a slight amount together with the dried powder.

The calcination step can be carried out in one stage, but it is preferable that the calcination include preliminary calcination and final calcination, the preliminary calcination be performed in a temperature range of 250 to 400° C., and the final calcination be performed in a temperature range of 550 to 800° C. The preliminary calcination and the final calcination may be carried out continuously, or after the preliminary calcination is completed, the final calcination may be carried out anew. In addition, each of the preliminary calcination and the final calcination may be divided into several stages.

The preliminary calcination is performed at a heating temperature in a range of 250° C. to 400° C., and preferably 300° C. to 400° C., preferably in an inert gas flow. The temperature is preferably held at a constant temperature in a temperature range of 250° C. to 400° C., but it does not matter if the temperature varies, or gently rises or decreases in the range of 250° C. to 400° C. The time for holding the heating temperature is preferably 30 minutes or longer, and more preferably 3 to 12 hours.

With respect to the temperature raising pattern until the time when the temperature reaches a preliminary calcination temperature, the temperature may be raised linearly, or the temperature may be raised in such a way as to draw an upward or downward convex arc.

The average temperature raising rate during raising temperature until the temperature reaches the preliminary calcination temperature is not particularly limited, but is generally about 0.1 to 15° C./min, preferably 0.5 to 5° C./min, and more preferably 1 to 2° C./min.

The final calcination is carried out at 550 to 800° C., preferably 580 to 750° C., more preferably 600 to 720° C., and still more preferably 620 to 700° C., preferably in an inert gas flow. The temperature is preferably held at a constant temperature in a temperature range of 620 to 700° C., but it does not matter if the temperature varies, or gently rises or decreases in the range of 620 to 700° C. The time for the final calcination is 0.5 to 20 hours, and preferably 1 to 15 hours.

In a case where the calcination pipe is divided with the weir plate or plates, the dried powder and/or the composite oxide catalyst consecutively pass through at least two, preferably 2 to 20, and more preferably 4 to 15 zones. The temperature control can be performed using one or more controllers, but the temperature is preferably controlled by installing a heater and a controller for every zone divided by the weir plates in order to obtain the desired calcination pattern. For example, in a case where seven weir plates are installed in such a way as to equally divide the length of a portion, which enters a heating furnace, of the calcination pipe into eight, and the calcination pipe divided into eight zones is used, the setting temperatures of the eight zones are preferably controlled with the heater and controller installed for the respective zones in such a way that the temperature of the dried powder and/or the composite oxide catalyst shows the desired calcination temperature pattern. It is to be noted that it does not matter if an oxidative component (for example, oxygen) or a reductive component (for example, ammonia) is added as desired to the calcination atmosphere in an inert gas flow.

With respect to the temperature raising pattern until the time when the temperature reaches a final calcination temperature, the temperature may be raised linearly, or the temperature may be raised in such a way as to draw an upward or downward convex arc.

The average temperature raising rate during raising temperature until the temperature reaches the final calcination temperature is not particularly limited, but is generally 0.1 to 15° C./min, preferably 0.5 to 10° C./min, and more preferably 1 to 8° C./min.

The average temperature decreasing rate after the completion of the final calcination is preferably 0.05 to 100° C./min, and more preferably 0.1 to 50° C./min. Holding the temperature temporarily at a temperature lower than the final calcination temperature is also preferable. The holding temperature is a temperature lower than the final calcination temperature by 10° C., preferably 50° C., and more preferably 100° C. The holding time is 0.5 hours or longer, preferably 1 hour or longer, more preferably 3 hours or longer, and still more preferably 10 hours or longer.

In a case where after the preliminary calcination is completed, the final calcination is carried out anew, a low-temperature treatment is preferably performed in the final calcination.

The time required for the low-temperature treatment, that is the time required until the temperature of the dried powder and/or the composite oxide catalyst is raised to the calcination temperature after the temperature is lowered can appropriately be adjusted by the size, thickness, and material of the calciner, the production amount of the catalyst, a series of periods of continuously calcining the dried powder and/or the composite oxide catalyst, the fixing rate/fixing amount, and the like. For example, in a case where a SUS calcination pipe with an inner diameter of 500 mm, a length of 4500 mm, and a thickness of 20 mm is used, the time required for the low-temperature treatment is preferably within 30 days, more preferably within 15 days, still more preferably within 3 days, and particularly preferably within 2 days during the series of periods of continuously calcining the catalyst.

For example, in a case where the dried powder is supplied at a rate of 35 kg/hr while the dried powder is being rotated at 6 rpm with a rotary furnace having a SUS calcination pipe with an inner diameter of 500 mm, a length of 4500 mm, and a thickness of 20 mm, and the final calcination temperature is set to 645° C., a step of lowering the temperature to 400° C. and then raising the temperature to 645° C. can be performed in about one day. In a case where the calcination is performed for one year continuously, by carrying out such a low-temperature treatment with a frequency of once per month, the calcination can be performed while the oxide layer temperature is being kept stable.

[Method for Producing Unsaturated Nitrile]

A method for producing an unsaturated nitrile of the present embodiment produces the unsaturated nitrile by subjecting propane or isobutane to gas-phase catalytic ammoxidation reaction in the presence of the oxide catalyst of the present embodiment.

(Starting Material)

Propane or isobutane, and ammonia, which are starting materials, do not necessarily have to be of high purity, and industrial grade gases such as propane containing 3 vol % or less of impurities such as ethane, ethylene, and n-butane, and ammonia containing 3 vol % or less of impurities such as water can be used. An oxygen-containing gas is not particularly limited, and for example, air, oxygen-enriched air, pure oxygen, a gas obtained by diluting any of these by an inert gas such as helium, argon, carbon dioxide, or nitrogen, or by steam can also be provided for the reaction. Among these, in a case where the oxygen-containing gas is used in an industrial scale, air is preferably used from the viewpoint of simplicity.

(Reaction Condition)

The gas-phase catalytic ammoxidation reaction of propane or isobutane can be performed under, for example, but not particularly limited to, the following conditions. The molar ratio of oxygen to be supplied for the reaction to propane or isobutane is preferably 0.1 to 6, and more preferably 0.5 to 4. The molar ratio of ammonia to be supplied for the reaction to propane or isobutane is preferably 0.3 to 1.5, and more preferably 0.7 to 1.2.

The reaction temperature is preferably 350 to 500° C., and more preferably 380 to 470° C. The reaction pressure is preferably $5 \times 10^4$ to $5 \times 10^5$ Pa, and more preferably $1 \times 10^5$ to $3 \times 10^5$ Pa. The contact time is preferably 0.1 to 10 sec·g/cm³, and more preferably 0.5 to 5 sec·g/cm³. By setting the conditions for the gas-phase catalytic ammoxidation reaction to the above-described ranges, there is a tendency that production of by-products is more suppressed and the yield of an unsaturated nitrile can be more improved.

In the present embodiment, the contact time is defined by the following equation.

Contact time(sec·g/cm³)=(W/F)×273/(273+T)

wherein W, F, and T are defined as follows.

W=amount (g) of catalyst filled

F=flow rate (Ncm³/sec) of starting material mixed gas in standard state (0° C., $1.013 \times 10^5$ Pa)

T=reaction temperature (° C.)

As a reaction system in the gas-phase catalytic ammoxidation reaction, a conventional system, such as a fixed bed, a fluidized bed, and a movable bed, can be adopted. Among these, a fluidized bed reactor with which removal of the heat of reaction is easy is preferable. The gas-phase catalytic ammoxidation reaction may be a single flow type or a recycle type.

EXAMPLES

Hereinafter, the present embodiment will be described in more detail giving specific Examples and Comparative Examples, but the present embodiment is not limited at all by the following Examples and Comparative Examples within a range not exceeding the gist of the present embodiment. Respective physical properties and evaluations performed in Examples and Comparative Examples, which will be mentioned later, were measured by the following methods.

Example 1

<Preparation Step a; Preparation of Aqueous Mixed Liquid ($A_1$)>

To 2572 g of water, 436.4 g of ammonium heptamolybdate [$(NH_4)_6Mo_7O_{24} \cdot 4H_2O$] and 54.6 g of ammonium metavanadate [$NH_4VO_3$], 91.4 g of diantimony trioxide [$Sb_2O_3$], and 5.4 g of cerium nitrate [$Ce(NO_3)_3 \cdot 6H_2O$] were added, and a resultant mixture was heated at 98° C. for 2 hours under stirring to prepare aqueous mixed liquid ($A_1$).

<Preparation Step B; Preparation of Niobium Starting Material Liquid ($B_1$)>

A niobium starting material liquid was prepared by the following method. In a mixing tank, 57.9 kg of water was added, and the water was then heated to 45° C. Thereafter, 72.2 kg of oxalic acid dihydrate [$H_2C_2O_4 \cdot 2H_2O$] was loaded under stirring, and 19.9 kg of niobic acid containing 76.0% by mass of $Nb_2O_5$ was subsequently loaded to mix the two in the water. This liquid was stirred under heating at 70° C. for 8 hours, and an aqueous mixed liquid was thereby obtained. This aqueous mixed liquid was left to stand and cooled with ice, and a solid was then filtrated and separated by suction filtration to obtain uniform niobium starting material liquid ($B_1$). The molar ratio of oxalic acid/niobium in this niobium starting material liquid was found to be 2.11 by the analysis described below. The obtained niobium starting material liquid was used as niobium starting material liquid ($B_1$) in production of oxide catalysts of Examples 2 to 5 described below.

The molar ratio of oxalic acid/niobium in niobium starting material liquid ($B_1$) was calculated as described below. After a heating treatment such that niobium starting material liquid ($B_1$) was stirred at 40° C. for 20 minutes after a lapse of one day from the preparation was carried out, and niobium starting material liquid ($B_1$) was left to stand still at 20° C. for 7 days from the heating treatment, the molar ratio of oxalic acid/niobium and the turbidity were measured.

The Nb concentration in the aqueous mixed liquid was calculated from the weight of solid $Nb_2O_5$ obtained in such a way that 10 g of niobium starting material liquid ($B_1$) was precisely weighed in a crucible, dried at 120° C. for 2 hours, and then subjected to a heating treatment at 600° C. for 2 hours to find that the Nb concentration was 1.072 mol/kg.

In a 300-mL glass beaker, 3 g of niobium starting material liquid ($B_1$) was precisely weighed, 20 mL of hot water of about 80° C. was added, and 10 mL of 1:1 sulfuric acid was subsequently added. A mixed liquid obtained in this way was titrated under stirring using 1/4N $KMnO_4$ while the liquid temperature was being kept at 70° C. in a water bath. The point where a faint, pale pink color due to $KMnO_4$ was continued about 30 seconds or longer was defined as the end point. The oxalic acid concentration was calculated from the titrated amount according to the following formula to find that the oxalic acid concentration was found to be 2.26 mol/kg.

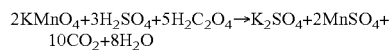

$$2KMnO_4 + 3H_2SO_4 + 5H_2C_2O_4 \rightarrow K_2SO_4 + 2MnSO_4 + 10CO_2 + 8H_2O$$

The turbidity was measured using 2100AN Turbidimeter manufactured by HACH after niobium starting material liquid ($B_1$) was left to stand still for one day from the preparation. In a measurement cell, 30 mL of the solution was placed to perform measurement based on US EPA method 180.1 to find that the turbidity of the niobium starting material liquid ($B_1$) was 69 NTU.

<Mixing Step; Preparation of Precursor Slurry ($C_1$)>

After the obtained aqueous mixed liquid ($A_1$) was cooled to 70° C., 593.8 g of silica sol containing 34.1% by mass of $SiO_2$ was added to the aqueous mixed liquid ($A_1$), and further at the time when the liquid temperature became 55° C., 181 g of a hydrogen peroxide solution containing 30% by mass of $H_2O_2$ was added to obtain aqueous mixed liquid ($A_1'$). Immediately after that, 309.1 g of niobium starting material liquid ($B_1$), 34.2 g (purity 50%) of an ammonium metatungstate aqueous solution, and a dispersion liquid obtained by dispersing 247.5 g of powder silica in 2228 g of water were added in sequence to aqueous mixed liquid ($A_1$), 51.7 g of 25% ammonia water was then added, and a resultant mixture was subjected to aging by stirring at 65° C. for 2.5 hours to obtain precursor slurry ($C_1$).

<Drying Step; Preparation of Dried Powder ($E_1$)>

The obtained precursor slurry ($C_1$) was supplied to a centrifugal spray drier and dried to obtain microspherical dried powder ($D_1$). Air was used as a heat source for drying. It is to be noted that the same heat source for drying was used in the centrifugal spray drier in the following Examples and Comparative Examples. The inlet temperature of the drier was 210° C., and the outlet temperature was 120° C. The resultant dried powder ($D_1$) was classified using a sieve having an opening of 32 m to obtain dried powder ($E_1$), which is a classified product.

<Calcination Step; Preparation of Oxide Catalyst ($F_1$)>

In a PYREX calcination pipe (PYREX is registered trade mark) having a diameter of 3 inches, 100 g of the resultant dried powder ($E_1$) was filled and was calcined at 685° C. for 2 hours under a nitrogen flow of 5.0 NL/min while the pipe was being rotated, and oxide catalyst ($F_1$) was thereby obtained.

<Removal Step>

In a vertical tube (inner diameter 41.6 mm, length 70 cm) provided with a holed disc with three holes having a diameter of 1/64 inches at the bottom portion and having a paper filter installed at the upper portion, 50 g of oxide catalyst ($F_1$) was loaded. Thereafter, air was allowed to flow upward from below in the vertical tube through the respective holes at room temperature to facilitate contact among the calcined bodies. The length of the air flow on that occasion in a direction to which the air flowed was 56 mm, and the average linear velocity of the air flow was 332 m/s. A protrusion did not exist in the obtained oxide catalyst ($F_1$) 24 hours later.

<Physical Property 1; Composition Analysis of Catalytically Active Species ($G_1$) by STEM-EDX In a 500-mL glass beaker, 200 g of a hydrogen peroxide solution containing 10% by mass of $H_2O_2$ was placed, and the water temperature was adjusted to 27° C. To this hydrogen peroxide solution, 15 g of oxide catalyst ($F_1$) after removing the protrusion was added and stirred using a magnetic stirrer at 500 rpm for 5 hours, and an insoluble component was then obtained by suction filtration. The obtained insoluble component was dried at 50° C. for 12 hours to collect residue (H1). The collected residue ($H_1$) was such that the other crystals other than catalytically active species ($G_1$) and the carrier (for example, silica) were removed by the oxidation treatment with the hydrogen peroxide solution, and contains catalytically active species ($G_1$) and the carrier.

The obtained residue ($H_1$) was ground with a mortar for 30 seconds to obtain a powder sample. In a vial bottle having an inner volume of 10 mL, 0.1 g of the obtained powder sample and 6 mL of an ethanol liquid were placed. The vial bottle was put in a tabletop ultrasonic washing machine (YAMATO BRANSON manufactured by Yamato Scientific Co., Ltd.) and vibrated by an ultrasonic for 60 seconds to disperse the powder sample of residue ($H_1$) in the ethanol liquid.

After that, this ethanol dispersion liquid of the powder sample was dropped onto a Cu mesh with a carbon support membrane (elastic carbon support membrane; grid pitch 100 μm; manufactured by Okenshoji Co., Ltd.), and the dropped liquid was then retained about one minute and was then removed using filter paper and the like. Thereby, a sample such that a catalyst particle in the dispersion liquid was put on the carbon support membrane of the Cu mesh was prepared. The sample prepared in this way was observed using STEM-EDX.

A scanning transmission electron microscope equipped with an energy dispersive characteristic X-ray spectrometer (STEM-EDX) was used for quantitative determination of catalytically active species ($G_1$) in the powder sample was used. HD2300 A (manufactured by Hitachi Hi-Tech Corporation) was used as the scanning transmission electron microscope (STEM), and Apollo XLT2 SUTW (manufactured by AMETEK, Inc) was used as the energy dispersive characteristic X-ray spectrometer (EDX). Genesis (Ver6.53, manufactured by AMETEK, Inc.) was used as software for EDX measurement and analysis.

The energy calibration method for EDX was as follows. A sample in which Al and Cu exist was used, and the sample was irradiated with an electron beam accelerated at 200 kV to detect characteristic X-rays. In the spectrum of characteristic X-rays detected on that occasion, a measurement place where the peak intensity of Al-Kα ray was about the same as or somewhat higher than the peak intensity of Cu-Kα ray, and the number of counts (CPS) became 1000 to 5000 cps was selected. Calibration of energy values was carried out using the Calibration function on the software, setting the number of times of measurement to 5, setting peak 1 to the energy value of Al-Kα ray (1.486 eV), and setting peak 2 to the energy value of Cu-Kα ray (8.04 eV).

The conditions for measuring the characteristic X-rays were as follows. Acceleration voltage was 200 kV, Operation Mode; Normal, the objective aperture was No. 2 (hole diameter 60 μm #, irradiation angle about 15 mrad), the angle of inclination of the spectrometer was 26°, an EDX aperture was inserted to measure a spectrum by area analysis in such a way as to include the periphery of the central portion of a catalyst particle. The measurement was conducted under EDX detection conditions of 7.68 μsec as the time constant and about 70 to 80 sec as the integral time.

A thin film correction method (Thin Apex) for STEM was used as a quantitative determination method. The quantitative determination was carried out using L rays for Nb, Mo, Sb, and W, and K rays for V. As K factors for use in the quantitative determination, the values registered on the software, Nb-L: 3.52, Mo-L; 3.62, Sb-L; 5.59, V-K; 1.34, and W-L; 7.68 (K factors which are recommendation values by the apparatus manufacturer; AMETEK EDAX), were used. The sample density for use in the quantitative determination was set to 7.8 g/cm³ (average density of Nb, Mo, Sb, and V), and the film thickness was set to 50 nm. The quantitative determination was performed setting background elimination to automatic setting.

The measurement was performed at 15 points, and the composition of catalytically active species ($G_1$) was calculated by taking an average of them. On that occasion, in a case where the carrier (for example, silica) was calculated as composition, the silica was excluded from the measurement result. A particle existing as a crystal in the sample was only catalytically active species ($G_1$) due to the above-mentioned oxidation treatment with a hydrogen peroxide solution. Accordingly, by observing a particle in which cross stripes which reflect periodicity of crystals are being observed among the observed particles in a visual field of observation, catalytically active species ($G_1$) can efficiently be found. The composition of catalytically active species ($G_1$) is shown in Table 1.

<Physical Property 2; Evaluation of Reaction in Ammoxidation Reaction of Propane>

Propane was provided for gas-phase catalytic ammoxidation reaction by the following method using oxide catalyst ($F_1$) obtained above. In a VYCOR glass fluidized bed type reaction pipe with an inner diameter of 25 mm, 40 g of the oxide catalyst was filled, and a mixed gas having a molar ratio of propane:ammonia:oxygen:helium=1:1.1:2.9:11.6 was supplied at a contact time of 3.0 (sec·g/cm³) under a reaction temperature of 445° C. and a reaction pressure of 40 kPa.

The yield of acrylonitrile was determined as follows. After a calibration curve was acquired in advance by analyzing a gas of acrylonitrile having a known concentration by gas chromatography (GC: product name "GC 2014" manufactured by SHIMADZU CORPORATION), a gas produced by the ammoxidation reaction was injected quantitatively in GC, and the number of moles of acrylonitrile produced was measured. The yield of acrylonitrile was determined from the number of moles of acrylonitrile measured according to the following equation.

Yield of acrylonitrile(%)=(number of moles of acrylonitrile produced)/(number of moles of propane supplied)×100

The reaction was continuously performed with this catalyst ($F_1$), and the reaction yield of acrylonitrile (AN) measured 10 days after starting the reaction is shown in Table 1.

<Physical Property 3; Measurement of Amount of Catalyst>

The amount of the catalyst was defined as the amount (% by mass) of the $SiO_2$ carrier based on the total amount (100% by mass) of oxide catalyst ($F_1$), and the obtained oxide catalyst ($F_1$) was pulverized/mixed for two hours using a uniaxial type agate automatic mortar (manufactured by NITTO KAGAKU CO., LTD.), and press-molded with a uniaxial press into a vinyl chloride ring (manufactured by Rigaku Corporation). Measurement with semi-quantitative analysis was performed on the obtained pellet by a fundamental-parameter (FP) method in which a content ratio is determined from the sensitivity library registered on the software in advance using wavelength dispersive X-ray fluorescence analysis (trade name "RIX 1000" manufactured by Rigaku Corporation, Cr tube, tube voltage 50 kV, tube current 50 mA). Mass proportion ($I_1$) (%) of the carrier (for example, silica), determined by the measurement, is shown in Table 1.

<Physical Property 4; Measurement of Composition and Amount of Catalytically Active Species by X-Ray Fluorescence Analysis>

Composition analysis with X-ray fluorescence was performed on a pellet obtained by pulverizing/mixing, in a mortar, residue ($H_1$) obtained in measuring physical property 1 to perform press-molding in the same manner as in Physical Property 3. Mass proportion ($J_1$) (%) of catalytically active species ($G_1$) assuming that the weight of the composite oxide was 100% can be calculated from the determined mass proportion ($I_2$) (%) of the carrier and mass ratio ($I_1$) (%) of the carrier in oxide catalyst ($F_1$), measured in Physical Property 3, using the following equation. The obtained mass proportion ($J_1$) (%) of the catalytically active species is shown in Table 1.

$$J_1 = \frac{100 \times (100 - I_2) \times I_1}{(100 - I_1) \times I_2}$$

Example 2

An oxide catalyst was prepared in the same manner as in Example 1, except that the addition amount of water was changed to 2564 g, the addition amount of ammonium heptamolybdate was changed to 440.9 g, the addition amount of ammonium metavanadate was changed to 52.2 g, the addition amount of diantimony trioxide was changed to 90.5 g, the addition amount of cerium nitrate was changed to 5.49 g, niobium starting material liquid ($B_1$) which was added was changed to 300.7 g in the preparation of aqueous mixed liquid ($A_1$), and the addition amount of the hydrogen peroxide solution was changed to 179.2 g, the addition amount of silica sol was changed to 593.8 g, the addition amount of the ammonium metatungstate aqueous solution was changed to 34.6 g, the addition amount of powder silica was changed to 247.5 g, and the addition amount of water was changed to 2228 g in the blending step for precursor slurry ($C_1$), and evaluations of physical properties 1 to 3 were performed by the same methods as in Example 1.

Example 3

An oxide catalyst was prepared in the same manner as in Example 1, except that the addition amount of water was changed to 2732 g, the addition amount of ammonium heptamolybdate was changed to 421.1 g, the addition amount of ammonium metavanadate was changed to 63.8 g, the addition amount of diantimony trioxide was changed to 76.1 g, the addition amount of cerium nitrate was changed to 5.25 g, niobium starting material liquid ($B_1$) which was added was changed to 176.8 g in the preparation of aqueous mixed liquid ($A_1$), and the addition amount of the hydrogen peroxide solution was changed to 192.3 g, the addition amount of silica sol was changed to 862.2 g, the addition amount of the ammonium metatungstate aqueous solution was changed to 33.0 g, the addition amount of powder silica was changed to 196.0 g, and the addition amount of water was changed to 1764 g in the blending step for precursor slurry ($C_1$), and evaluations of physical properties 1 to 3 were performed by the same methods as in Example 1.

Example 4

An oxide catalyst was prepared in the same manner as in Example 1, except that the addition amount of water was changed to 2909 g, the addition amount of ammonium heptamolybdate was changed to 448.3 g, the addition amount of ammonium metavanadate was changed to 67.9 g, the addition amount of diantimony trioxide was changed to 84.7 g, the addition amount of cerium nitrate was changed to 5.6 g, niobium starting material liquid ($B_1$) which was added was changed to 211.7 g in the preparation of aqueous mixed liquid ($A_1$), and the addition amount of the hydrogen peroxide solution was changed to 166.7 g, the addition amount of silica sol was changed to 791.8 g, the addition amount of the ammonium metatungstate aqueous solution was changed to 35.2 g, the addition amount of powder silica was changed to 180.0 g, and the addition amount of water was changed to 1620 g in the blending step for precursor slurry ($C_1$), and evaluations of physical properties 1 to 3 were performed by the same methods as in Example 1.

Example 5

An oxide catalyst was prepared in the same manner as in Example 1, except that the ammonium metatungstate aqueous solution was not added in the blending step for precursor slurry ($C_1$), and evaluations of physical properties 1 to 3 were performed by the same methods as in Example 1.

Example 6

Aqueous mixed liquid ($A_1$) was prepared in the same manner as in Example 1, except that water was changed to 25 kg, ammonium heptamolybdate [$(NH_4)_6Mo_7O_{24} \cdot 4H_2O$] was changed to 4.088 kg, ammonium metavanadate [$NH_4VO_3$] was changed to 0.646 kg, diantimony trioxide [$Sb_2O_3$] was changed to 0.907 kg, and cerium nitrate was changed to 0.051 kg, and a resultant mixture was heated at 95° C. for 1 hour under stirring in the preparation of aqueous mixed liquid ($A_1$).

Niobium starting material liquid ($B_1$) was prepared in the same manner as in Example 1, except that an aqueous mixed liquid obtained by changing water to 77.3 kg, oxalic acid dihydrate [$H_2C_2O_4 \cdot 2H_2O$] to 57.0 kg, and niobic acid to 15.7 kg, and stirring a resultant mixture under heating at 73° C. for 6 hours was cooled to 40° C. by natural cooling under stirring in the preparation of niobium starting material liquid ($B_1$).

The molar ratio of oxalic acid/niobium and the turbidity of niobium starting material liquid ($B_2$) were measured in the same manner as in Example 1. As a result, it was found that the Nb concentration was 0.756 mol/kg, the oxalic acid concentration was 1.74 mol/kg, and the turbidity was 32 NTU.

After the obtained aqueous mixed liquid ($A_1$) was cooled to 70° C., 7.038 kg of silica sol containing 34.0% by mass of $SiO_2$ was added, 1.06 kg of a hydrogen peroxide solution containing 30% by mass of $H_2O_2$ was further added to the aqueous mixed liquid ($A_1$), and stirring was continued at 55° C. for 30 minutes. After a dispersion liquid obtained by dispersing 3.850 kg of niobium starting material liquid ($B_1$) and 2.4 kg of powder silica (trade name "AEROSIL 200", manufactured by NIPPON AEROSIL Co., Ltd.) in 197.6 kg of water, and 0.319 kg of an ammonium metatungstate liquid containing 50.2% by weight of tungsten oxide were further added to the liquid in sequence, a resultant mixture was stirred at 50° C. for 2.5 hours to obtain precursor slurry ($C_1$).

An oxide catalyst was prepared in the same manner as in Example 1 excluding those described above, and evaluations of physical properties 1 to 3 were performed by the same methods as in Example 1.

Example 7

An oxide catalyst was prepared in the same manner as in Example 6, except that water was changed to 83.2 kg, oxalic acid dihydrate [$H_2C_2O_4 \cdot 2H_2O$] was changed to 52.3 kg, and niobic acid was changed to 14.5 kg, and a resultant mixture was stirred under heating at 78° C. for 5 hours in the preparation of niobium starting material liquid ($B_1$), and evaluations of physical properties 1 to 3 were performed by the same methods as in Example 1.

The molar ratio of oxalic acid/niobium and the turbidity of the obtained niobium starting material liquid ($B_1$) were measured in the same manner as in Example 1. As a result, it was found that the niobium concentration was 0.753 mol/kg, the oxalic acid concentration was 1.77 mol/kg, and the turbidity was 41 NTU.

Comparative Example 1

In a mixing tank, 88.7 kg of water was added, and the water was then heated to 50° C. Thereafter, 48.1 kg of oxalic acid dihydrate [$H_2C_2O_4 \cdot 2H_2O$] was loaded under stirring, and 13.2 kg of niobic acid containing 76.3% by mass of $Nb_2O_5$ was subsequently loaded to mix the two in the water. An aqueous mixed liquid obtained by subjecting this liquid to stirring under heating at 95° C. for 3 hours was cooled to 40° C. by natural cooling under stirring. The aqueous mixed liquid was then cooled to 2° C. at −10° C./hr and was left to stand for 1 hour. Thereafter, a mixture of a deposited solid and the mixed liquid was poured into a filter, and a mixed liquid was obtained by filtrating the deposited solid.

An oxide catalyst was prepared in the same manner as in Example 1, except that the resultant mixed liquid was used as niobium starting material liquid ($B_1$), and evaluations of physical properties 1 to 3 were performed by the same methods as in Example 1. The analysis of the obtained niobium starting material liquid ($B_1$) was performed in the same manner as in Example 1 to find that the Nb concentration of this niobium starting material liquid ($B_1$) was 0.578 mol/kg, the molar ratio of oxalic acid/niobium was 2.77, and the turbidity was 201 NTU.

Comparative Example 2

An oxide catalyst was prepared in the same manner as in Example 3, except that preparation was performed using niobium starting material liquid ($B_1$) prepared in the same manner as in Comparative Example 1, and evaluations of physical properties 1 to 3 were performed by the same methods as in Example 1.

Comparative Example 3

An oxide catalyst was prepared in the same manner as in Example 5, except that preparation was performed using niobium starting material liquid ($B_1$) prepared in the same manner as in Comparative Example 1, and evaluations of physical properties 1 to 3 were performed by the same methods as in Example 1.

Example 8

An oxide catalyst was prepared in the same manner as in Example 1, except that the amount of water loaded was changed to 67.5 kg, oxalic acid dihydrate [$H_2C_2O_4 \cdot 2H_2O$] was changed to 64.6 kg, niobic acid was changed to 17.9 kg, and a resultant mixture was stirred under heating at 95° C. for 4 hours in the preparation of niobium starting material liquid ($B_1$), and evaluations of physical properties 1 to 3 were performed by the same methods as in Example 1.

Comparative Example 4

An oxide catalyst was prepared in the same manner as in Example 6, except that preparation of niobium starting material liquid ($B_1$) was performed in the same manner as in Example 8, and evaluations of physical properties 1 to 3 were performed by the same methods as in Example 1.

TABLE 1

|   | Composition of active species ($G_1$) | Amount of silica carrier $I_1$ (%) | Amount of catalytically active species $J_1$ (%) | Acrylonitrile yield (%) |
|---|---|---|---|---|
| Example 1 | $Mo_1V_{0.125}Sb_{0.112}Nb_{0.200}W_{0.054}$ | 48.5 | 48.7 | 56.8 |
| Example 2 | $Mo_1V_{0.095}Sb_{0.098}Nb_{0.185}W_{0.052}$ | 48.6 | 52.5 | 57.0 |
| Example 3 | $Mo_1V_{0.140}Sb_{0.076}Nb_{0.175}W_{0.051}$ | 52.1 | 43.4 | 56.0 |
| Example 4 | $Mo_1V_{0.120}Sb_{0.103}Nb_{0.196}W_{0.053}$ | 48.3 | 43.1 | 56.2 |
| Example 5 | $Mo_1V_{0.123}Sb_{0.110}Nb_{0.198}W_{0.00}$ | 48.4 | 48.5 | 56.7 |
| Example 6 | $Mo_1V_{0.121}Sb_{0.108}Nb_{0.151}W_{0.048}$ | 48.2 | 44.5 | 56.2 |
| Example 7 | $Mo_1V_{0.128}Sb_{0.089}Nb_{0.162}W_{0.051}$ | 48.2 | 44.3 | 56.2 |
| Example 8 | $Mo_1V_{0.124}Sb_{0.098}Nb_{0.160}W_{0.049}$ | 48.3 | 44.2 | 56.3 |
| Comparative Example 1 | $Mo_1V_{0.143}Sb_{0.020}Nb_{0.212}W_{0.051}$ | 48.6 | 15.8 | 35.0 |
| Comparative Example 2 | $Mo_1V_{0.153}Sb_{0.056}Nb_{0.106}W_{0.051}$ | 51.9 | 30.6 | 53.0 |
| Comparative Example 3 | $Mo_1V_{0.199}Sb_{0.082}Nb_{0.097}W_{0.00}$ | 48.2 | 25.8 | 52.0 |
| Comparative Example 4 | $Mo_1V_{0.154}Sb_{0.075}Nb_{0.144}W_{0.047}$ | 48.2 | 40.5 | 55.0 |

The invention claimed is:

1. An oxide catalyst to be used for gas-phase catalytic ammoxidation reaction of propane or isobutane, the oxide catalyst comprising a composite oxide, wherein
the composite oxide comprises a catalytically active species to be isolated from the composite oxide using a hydrogen peroxide solution, and
the catalytically active species has an average composition represented by the following formula (1) in STEM-EDX measurements;

Formula:

$$Mo_1V_aSb_bNb_cW_dX_eO_n \qquad (1)$$

wherein X represents at least one selected from the group consisting of Te, Ce, Ti, and Ta; a, b, c, and d satisfy relations represented by formulae of 0.050≤a≤0.200, 0.050≤b≤0.200, 0.100≤c≤0.300, 0≤d≤0.100, 0≤e≤0.100, and a≤c; and n represents a number determined by valences of the other elements; and wherein a mass proportion of the catalytically active species is 45% by mass or more based on a total amount of the composite oxide.

2. The oxide catalyst according to claim 1, wherein the formula (1) satisfies a relation represented by a formula of 1.1×a≤c.

3. The oxide catalyst according to claim 1, wherein the formula (1) satisfies a relation represented by a formula of 1.3×a≤c.

4. The oxide catalyst according to claim 1, wherein the formula (1) satisfies a relation represented by a formula of 8.00≤100×b/(1+a)≤10.00.

5. The oxide catalyst according to claim 1, further comprising silica as a carrier carrying the composite oxide, and
a mass proportion of the silica is 30 to 70% by mass in terms of $SiO_2$ based on a total amount of the oxide catalyst.

6. A method for producing an unsaturated nitrile, the method comprising producing an unsaturated nitrile through gas-phase catalytic ammoxidation reaction of propane or isobutane in the presence of the oxide catalyst according to claim 1.

7. The oxide catalyst according to claim 1, produced by a method comprising:

a preparation step B of mixing a niobium starting material and an organic acid, thereby preparing a niobium starting material liquid B;

wherein a molar ratio of the organic acid to Nb (organic acid/Nb) to 2.40 or less, in the niobium starting material liquid B.

8. The oxide catalyst according to claim 7, wherein a mixing temperature in preparation step B is 80° C. or less.

9. The oxide catalyst according to claim 7, wherein a turbidity of the niobium starting material liquid B is 500 NTU or less.

10. The oxide catalyst according to claim 7, wherein a mixing temperature in preparation step B is higher than 60° C. and lower than 80° C.

11. The oxide catalyst according to claim 7, wherein the preparation step B is carried out in 1 hour or longer and 8 hours or shorter.

* * * * *